US00PP08073P

United States Patent [19]

Walters, deceased

[11] Patent Number: Plant 8,073

[45] Date of Patent: Dec. 22, 1992

[54] VARIETY OF GERANIUM NAMED DUKE

[75] Inventor: Ernest Walters, deceased, late of Hucknall, Great Britain, by Mary Bodill, administrator

[73] Assignee: Oglevee, Ltd., Connellsville, Pa.

[21] Appl. No.: 700,211

[22] Filed: May 13, 1991

[51] Int. Cl.[5] ..... A01H 5/00

[52] U.S. Cl. ..... Plt./87.12

[58] Field of Search ..... Plt./68, 87.12

*Primary Examiner*—Howard J. Locker

*Attorney, Agent, or Firm*—Webb, Burden, Ziesenheim & Webb

[57] ABSTRACT

The variety is characterized by its bright, fluorescent red-maroon flowers which are bi-colored in appearance. The variety is sturdy with a compact mound and roots easily.

1 Drawing Sheet

BACKGROUND OF THE INVENTION

The present invention comprises a new and distinct cultivar of *Pelargonium*×*domesticum* known by the varietal name Duke (Oglevee No. 408; Walters No. 14W-O). The new variety was discovered by Mr. Ernest Walters in a selected breeding program in Hucknall, Nottingham, Great Britain. The new variety is a selection from the crossing of *P. citrosum*×*quercifolium*×Lady Mary Fox. The new variety was first asexually reproduced in the United States by cuttings at Oglevee, Ltd., Connellsville, Pa. in January of 1987. The new variety has been asexually reproduced by cuttings at Oglevee, Ltd. in Connellsville, Pa. over a several year period. It has also been trialed at Connellsville and has been found to retain its distinctive characteristics through successive propagations.

The cultivar when grown in a glass greenhouse in Connellsville, Pa. using natural light and 60° F. night and 68° F. day has a response time of 14 weeks from a rooted cutting, once pinched, to flowering in a 6 inch pot. The response time was determined on plants grown in soilless media employing constant fertilizer 150–200 parts per million of nitrogen and potassium in full light. The rooted cuttings were potted on Sep. 24, 1990 and flowered on Jan. 4, 1991.

DESCRIPTION OF THE DRAWING

The accompanying photographic drawing illustrates the new cultivar, with the colors set forth therein being as nearly true as possible with color illustrations of this type.

DESCRIPTION OF THE NEW PLANT

The following detailed description sets forth the characteristics of the new cultivar. The data which defines these characteristics were collected by asexual reproductions carried out by Oglevee, Ltd. in Connellsville, Pa. The plant history was taken on fourteen week plants blossomed under natural light in a greenhouse and the color readings were taken indoors under 200–220 foot candles of florescent cool white light. Color references are primarily to the R.H.S. Colour Chart of The Royal Horticultural Society of London.

THE PLANT

Classification:

*Botanical.*—*Pelargonium*×*domesticum.*

*Commercial.*—Regal geranium.

Form: Compact mound.

*Height.*—16.5 cm from media surface.

*Growth.*—Strong controlled wiry habit.

Strength: Ease of rooting; sturdy plant can withstand postharvest handling abuse.

Foliage: Stalked leaf attachment.

Leaves:

*Size.*—6.5 cm to 7.0 cm across.

*Shape.*—Depressed ovate. Base: Reniform.

*Margin.*—Serrately lobed.

*Texture.*—Leathery; pubescent.

*Color.*—Top: Green Group 137B. Bottom: Green Group 137C.

Ribs and veins.—Palmate venation. Color: Yellow/Green Group 147C.

Petioles:

*Color.*—Green Group 137C.

*Length.*—4.8 cm to 9.0 cm.

Stem:

*Color.*—Yellow/Green Group 146B.

*Internodes.*—1.0 cm to 2.0 cm in length.

THE BUD

Shape: Elliptical.

Size: 1.0 cm to 2.0 cm in length; bud just beginning to show color.

INFLORESCENCE

Blooming habit: Continuous; slow to shatter.

Size: 7.0 cm to 8.0 cm across at widest point.

Borne: Florets on pedicel; pedicel on peduncle.

Florest:

*Form.*—Cupped.

*Color.*—Top: Upper two petals — Red/Purple Group 60 B with a blotch of Greyed/Purple Group 187A and veining of Greyed/Purple Group 187A. Lower three petals — Red/Purple Group 61B with a blotch of Greyed/Purple Group 187B and veining of Red/Purple Group 60C. Throat — White Bottom: Red/Purple Group 65D.

*Petals.*—Five in number; separate, not united; margin entire.

*Size.*—4.5 cm to 5.0 cm across; fully open.

*Texture and appearance.*—Smooth, satin-like; appearance from a distance is a maroon bi-color with the top two petals darker than the bottom three; has "fluorescent glow".

Petaloids: None present.

Pedicel:

*Length.*—1.5 cm to 2.0 cm.

*Color.*—Yellow/Green Group 146B.

Peduncle: 4.0 cm to 5.5 cm in length.

*Color.*—Yellow/Green Group 146A.

Lasting quality: Slow to shatter.

REPRODUCTIVE ORGANS

Stamens:

*Anthers.*—3.0 mm to 4.0 mm in length; 5 to 7 in number.

*Filaments.*—1.6 cm to 2.0 cm in length. Color: White.

*Pollen.*—Greyed/Orange Group 172B.

Pistils:

*Number.*—1.

*Length.*—1.7 cm to 2.0 cm.

*Stigma.*—5 to 6 parted; Red/Purple.

*Style.*—1.3 cm; Red/Purple Group 60B.

Ovaries: 6.0 to 7.0 mm in length; light green, very pubescent.

Fruit: None observed.

GENERAL CHARACTERISTICS

This new variety of *Pelargonium*×*domesticum* is an improvement over the current Regal geraniums in the red color class. While this variety is not as true a red as Grand Slam or the Vavra Shirley, its other qualities make it by far more outstanding. Duke exhibits a show of bright (almost a fluorescent glow), red-maroon flowers on a neat compact plant. Cutting production is improved because of ease of branching. Rooting is quicker and easier than the varieties currently available.

I claim:

1. A new and distinct variety of geranium plant substantially as shown and described.

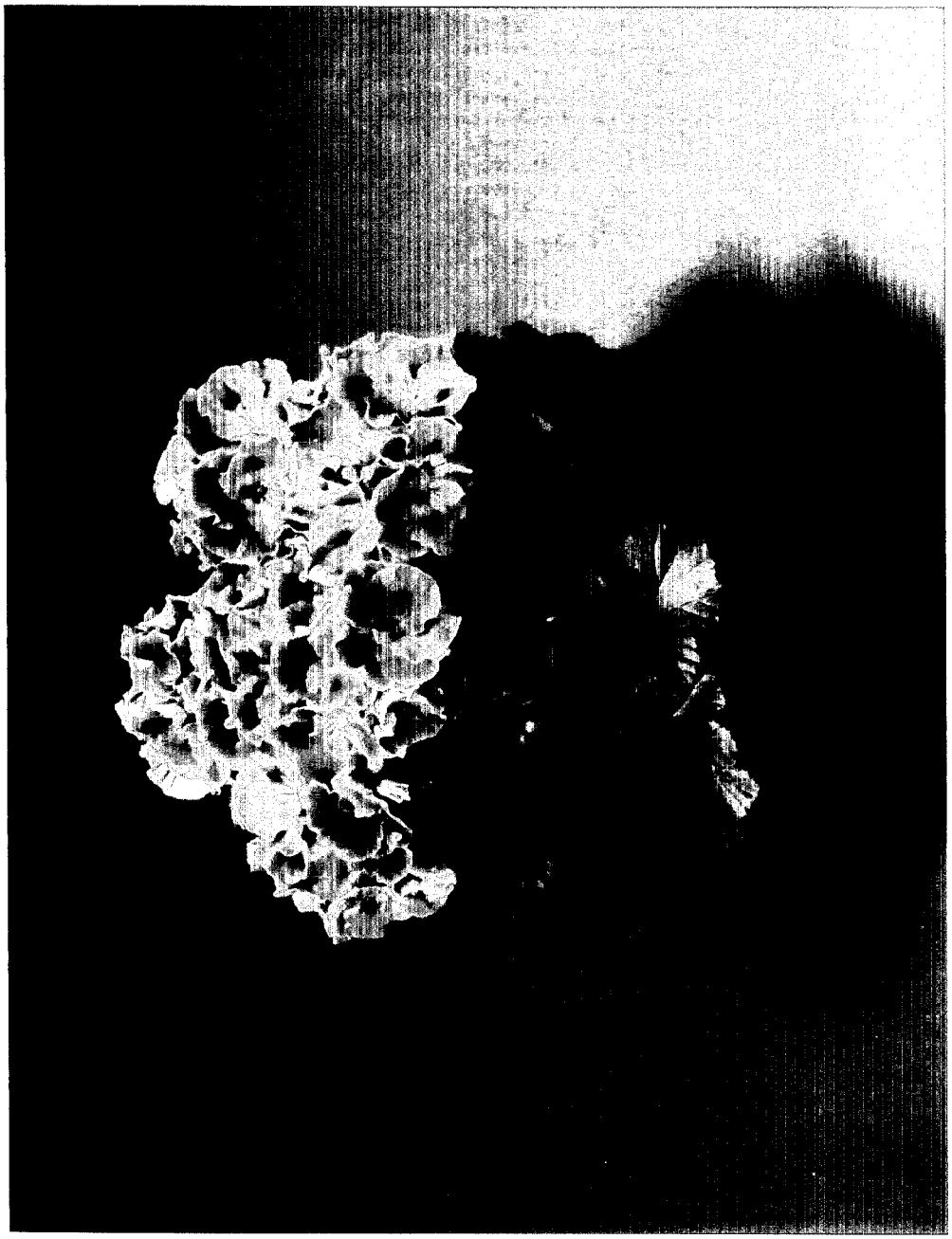

* * * * *